United States Patent
Gros et al.

(10) Patent No.: US 6,207,437 B1
(45) Date of Patent: *Mar. 27, 2001

(54) CRYSTALLINE PROTEASE AND METHOD FOR PRODUCING SAME

(75) Inventors: Ernst Hakan Gros, Kantvik; Jerry L. Cunefare, Espoo, both of (FI)

(73) Assignee: Genencor International, Inc., Palo Alto, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/615,343

(22) Filed: Mar. 11, 1996

(51) Int. Cl.[7] .............................. C12N 9/50; C12N 9/58; C12N 9/56; C30B 29/58
(52) U.S. Cl. ...................... 435/220; 117/927; 435/222; 435/223
(58) Field of Search .................... 435/220, 222, 435/223; 117/927, 56

(56) References Cited

U.S. PATENT DOCUMENTS

| | | | |
|---|---|---|---|
| 3,622,458 | * 11/1971 | Murao | 435/222 |
| 3,871,963 | * 3/1975 | Tobe et al. | 435/221 |
| 3,923,650 | * 12/1975 | Howe | 210/639 |
| 3,930,954 | * 1/1976 | Irie | 435/221 |
| 4,052,262 | * 10/1977 | Horikoshi et al. | 435/221 |
| 4,198,479 | * 4/1980 | Tytell et al. | 435/70.5 |
| 5,041,377 | * 8/1991 | Becker et al. | 435/220 |
| 5,073,487 | * 12/1991 | Lloyd | 435/23 |
| 5,126,115 | * 6/1992 | Fujita et al. | 117/206 |
| 5,405,767 | * 4/1995 | Shetty et al. | 435/195 |
| 5,437,993 | * 8/1995 | Visuri | 435/234 |
| 5,618,710 | * 4/1997 | Navia et al. | 435/174 |

FOREIGN PATENT DOCUMENTS

| | | |
|---|---|---|
| 0193 046 A2 | 3/1986 | (EP) . |
| 506866 | * 12/1990 | (EP) . |
| WO 89/08703 A1 | 9/1989 | (WO) . |
| WO 91/09943 A1 | 7/1991 | (WO) . |
| WO 92/09687 A1 | 6/1992 | (WO) . |
| WO 95/01989 A1 | 1/1995 | (WO) . |

OTHER PUBLICATIONS

Jencks (1987) Catalysis in Chemistry and Enzymology, Dover Publications, Inc., New York, pp. 358–360.*
Creighton (1993) Proteins Structures and Molecular Properties, W.H. Freeman and Co., New York, pp. 155–156.*
CRC Handbook of Chemistry and Physics (1970), The Chemical Rubber Co., Cleveland, p. D–240.*
Neurath (1984) Science, 224, "Evolution of Proteolytic Enzymes", pp. 350–357.*
M. Ottesen et al., "The Subtilisins", *Method in Enzymology*, vol. 19, 1970, pp. 199–215.
A. Mukhopadhyay, et al., "Treatment and Clarification of Fermented Broth in Bacterial Enzyme Production," Database Biosis Biosciences Information Service, *Biotechnol. Tech.* 4 (2), 1990, pp. 121–126 (see Abstract).

* cited by examiner

*Primary Examiner*—Jon P. Weber
(74) *Attorney, Agent, or Firm*—Genenecor International, Inc.

(57) ABSTRACT

A method for preparing a crystalline protease is provided which comprises preparing an aqueous solution containing the protease enzyme and adding to the aqueous solution sodium sulfate, allowing the crystallization to take place at a temperature between 10° C. and 60° C.

21 Claims, No Drawings

CRYSTALLINE PROTEASE AND METHOD FOR PRODUCING SAME

BACKGROUND OF THE INVENTION

The present invention is related to the crystallization of protease enzyme at a temperature greater than 10° C. More particularly, the present invention relates to selective crystallization of protease enzyme in an aqueous solution using sodium sulfate.

Intensive research efforts have been directed to the precipitation and crystallization of enzymes as a means of purification and preparation of enzyme products. For example, in U.S. Pat. No. 4,659,667, a process is disclosed for the recovery of an enzyme from solution by concentrating to supersaturation the enzyme-containing solution at pH near the isoelectric point of the enzyme, inducing crystallization and recovering the crystallized final product. Inducing crystallization is achieved by allowing the enzymes to spontaneously crystallize upon concentration or by seeding, sound, stirring or scratching the inner surface of the container. Crystallization of alpha-amylase is exemplified.

In PCT Publication No. WO 89/08703, a process is described for the crystallization of subtilisin by adding a halide salt, such as sodium chloride or calcium chloride, to a concentrated subtilisin solution of at least about 40 grams per liter.

In EP 506,866, a method for the crystallization of enzymes is disclosed which is characterized by using as a starting material an aqueous solution containing liquid with a relatively high enzyme purity and a concentration of enzyme of about at least 5 grams per liter and adding as a crystallization agent an easily soluble salt of the non-halide type to a concentration which is considerably smaller than the amount necessary to precipitate the enzymes in an amorphous form. Crystallization of certain subtilisin enzymes at temperatures up to 30° C. is exemplified. Sodium sulfate is used to help purify the protease product but not for crystallization.

In spite of these advances in the field of enzyme crystallization, inexpensive and efficient crystallization of proteases suitable for large scale production has remained problematic in industry. The ability to use room temperature and an inexpensive salt for industrial scale crystallization of protease would represent a large savings and be of great importance to the industry.

SUMMARY OF THE INVENTION

It is an object of the present invention to provide for a simple and low-cost method which crystallizes proteases.

One embodiment of the present invention provides a method for the crystallization of protease enzyme comprising (a) preparing an aqueous solution containing the protease enzyme; and (b) adding to the aqueous solution a salt comprising sodium sulfate, wherein said step (b) is carried out at a temperature between 10° C. and 60° C.

Through the practice of the present invention, it is possible to obtain in short periods of time a highly purified crystalline protease product which has exceptional yield characteristics. In fact, by optimizing conditions according to the present invention, it is often possible to obtain consistent yields of greater than 50%, and in a particularly preferred embodiment, yields of greater than 70–80% in a period of five hours. This result is of great value to the industry.

Yet another advantage of the present invention is that the crystallization process occurs very quickly. In contrast to many prior art processes which often require as much as 2–3 weeks for the crystallization of enzyme, the instant invention produces a high yield of highly purified protease crystals in as little as 5 hours.

Further, the method of the present invention is easily scaled to an industrial level.

DETAILED DESCRIPTION OF THE INVENTION

"Protease" or "protease enzyme" means proteins which have proteolytic activity and are generally found in enzyme class 3.4. Proteases which can be crystallized according to the present invention include serine proteases, thiol proteases, carboxyl or acid proteases, and metalloproteases.

In a preferred embodiment of the present invention, a method for the crystallization of protease enzyme is provided comprising preparing an aqueous solution containing said protease enzyme and adding to said aqueous solution a salt comprising sodium sulfate, wherein the aqueous solution is at a temperature of between about 10° C. and 60° C.

The protease enzyme of the invention can be obtained from any protease producing microorganism. Proteases which are preferably crystallized according to the present invention are derived from bacterial, fungal, plant and animal sources. More preferably, the bacterial proteases are derived from Bacillus sp., including *Bacillus amyloliquefaciens, Bacillus subtilis, Bacillus licheniformis, Bacillus lentus*, Thermomonospora sp., Pseudomonas sp., Clostridium sp., Streptomyces sp. and Micrococcus sp. As used herein, the term "Bacillus" or "Bacillus sp." refers to any bacterial strains which have previously been classified as Bacillus or which are currently classified as Bacillus. Preferred fungal proteases can be derived from Aspergillus sp. or Trichoderma sp. Preferred animal proteases are derived from bovine sp.

Genetically modified proteases which are derived from a DNA sequence in which one or more of the amino acids of the protease have been deleted, replaced or otherwise manipulated are also considered within the scope of the invention. Such modified proteases are described in, for example, PCT Publication No. WO 95/10615 and U.S. Pat. No. 5,185,258.

The fermentation procedures for culturing cells and for production of protease are known per se in the art. For example, protease enzyme can be produced either by solid or submerged culture, including batch, fed-batch and continuous-flow processes. The collection and purification of the protease enzyme from the fermentation broth can also be effected by procedures known per se in the art.

The aqueous solution which acts as starting material for the method according to the invention is derived from the fermentation broth produced by the fermentation of an appropriate microorganism. The fermentation broth will generally contain cellular debris including cells, various suspended solids and other biomass contaminants, as well as the desired protease product, which are preferably removed from the fermentation broth by means known in the art. Suitable processes for such removal include conventional solid-liquid separation techniques such as, e.g., centrifugation, filtration, dialysis, microfiltration, rotary vacuum filtration, or other known processes, to produce a cell-free filtrate. While it is contemplated as within the scope of the invention to crystallize the protease enzyme either directly from the fermentation broth or from the cell-free filtrate, it is preferable to further concentrate the fermentation broth or the cell free filtrate prior to crystallization using techniques such as ultrafiltration, evaporation, or precipitation.

It has long been known in the art that certain constituents, if included in a culture medium, will result in difficulty in crystallization of the component enzymes. For this reason, it is often advantageous to further purify the filtered fermentation broth to remove impurities which may interfere with crystallization by, for example, subjecting the filtered broth to column purification. Additionally, it is possible to limit the amount of such impurities by controlling the culture medium in which the microorganism is grown. For example, as described in Northrup et al. (1948) Crystalline Enzymes, Columbia University Press, p. 254, mucin-like substances, e.g., polysaccharides, are often detrimental to crystallization processes. Thus, by eliminating such polysaccharide components from the prefermentation culture medium or purifying such components from a fermentation broth, it is possible to improve the success of the subsequent crystallization. Alternatively, these substances can be removed by treatment of the filtrate with a strong acid, copper hydroxide, alcohol or acetone. Preferably, aluminum sulfate is used in purifying protease-containing fermentation broths in order to facilitate crystallization.

After preparation of the aqueous solution containing a protease enzyme, sodium sulfate is added to the aqueous solution, which is at a temperature between 10° C. and 60° C., more preferably between 20° C. and 40° C. and most preferably between 22° C. and 30° C., to initiate crystallization of the protease. It is preferred that the fermentation broth is treated with aluminum sulfate prior to crystallization. In a preferred embodiment, the protease concentration in the aqueous solution is between about 20 g/l and 80 g/l, more preferably between about 40 g/l and 60 g/l and most preferably between about 45 g/l and 52 g/l.

The sodium sulfate is added to the aqueous solution in a quantity and under conditions which are suitable to crystallize the protease enzyme. Such conditions, including temperature, pH, concentration of protease, concentration of sodium sulfate and incubation time, are easily ascertained by one of skill in the art through routine experimentation. However, in a preferred embodiment of the present invention, the sodium sulfate is added to the aqueous solution in a concentration of between about 0.5% and 10.0% w/v, more preferably between about 1% and 7.5% and most preferably between about 1.5% and 4.0%. The temperature of the aqueous solution after addition of the sodium sulfate is preferably between about 10° C. and 60° C., more preferably between about 20° C. and 40° C. and most preferably between about 22° C. and 30° C. The pH of the aqueous solution after the addition of the sodium sulfate is preferably between about 4 and 10, more preferably between about 5 and 9 and most preferably between about 4.8 and 5.4. Preferably the aqueous solution containing the sodium sulfate is incubated to maximize the production of crystalline protease for a period of between about 1 hour and 10 days, more preferably for a period of between about 2 hours and 48 hours and most preferably for a period of between about 5 hours and 24 hours.

Separation and collection of the crystalline protease from the aqueous solution after incubation can be achieved through any art recognized means for performing such separation. Suitable means include centrifugation, filtration, vacuum filtration and microfiltration.

Although not required, protease seed crystals can be added to the solution to facilitate improved crystallization kinetics and control reaction rate and crystal size distribution. As is well known in the art, the use of seed crystals results in favorable kinetics of the crystallization and may increase overall yield, depending on the reaction conditions selected. Crystallization may also be improved by providing crystallization vessels having surface properties conducive to crystallization, e.g., having scratches or notches on the inside wall of the vessel or other properties are well known to one of skill in the art. The use of the minimum but effective amount of seed crystals for a given protease solution, considering the size of the operation and process conditions will be apparent to one of skill in the art and should follow as in conventional crystallization processes. Crystal growth can be further promoted by providing gentle agitation of the crystallization vessel.

Crystalline protease produced by the method of the present invention can be used in a detergent composition according to methods well known in the art. Further, crystalline protease produced by the method of the present invention can be used in the preparation of a feed additive or in food preparation according methods well known in the art.

EXPERIMENTAL

Example 1

Crystallization of a Mutant Protease from *Bacillus subtilis*

An aqueous solution comprising an ultrafiltrate concentrate of a fermentation broth of a mutant protease derived from the fermentation of *Bacillus subtilis* was prepared. Methods for preparing mutant protease suitable for the present purpose are described in PCT Publication No. 95/10615. Ultrafiltration was carried out with a polysulfone membrane having a 10 Kd molecular weight cut off in a spiral ultrafiltration unit. The resultant protease solution was at a concentration of about 45 g/l. The protease concentration can be determined by the method described in Estell et al. (1985) *J. Biol. Chem.* 260:6518–6521.

The pH of the aqueous solution was adjusted to 5.3 using 33% formic acid. A 500 ml batch was stirred at 100 rpm with an agitator and sodium chloride was added to a concentration of 80 g/l. The batch was placed at 4° C. for three days then heated to 40° C. in 1.5 hours and kept at 40° C. for 1 hour, then the temperature was decreased to 4° C. for another three days. There was no crystallization during the first three days at 4° C. After raising the temperature to 40°, rapid crystal growth was observed under the microscope. After going back to 4° C., the crystal growth stopped. As can be seen, for protease, higher temperature promotes fast growth of crystals.

Example 2

Crystallization of a Mutant Protease from *Bacillus subtilis*

An aqueous solution comprising an ultrafiltrate concentrate of a fermentation broth of a mutant protease derived from the fermentation of *Bacillus subtilis* was prepared. Methods for preparing mutant protease suitable for the present purpose are described in U.S. Pat. No. 5,185,258. Ultrafiltration was carried out with a polysulfone membrane having a 10 Kd molecular weight cut off in a spiral ultrafiltration unit. The resultant protease solution was at a concentration of about 52 g/l of active enzyme. The protease concentration can be determined by the method described in Estell et al. (1985) *J. Biol. Chem.* 260:6518–6521.

The pH of the aqueous solution was adjusted to 5.5 using 33% formic acid. An 18 l batch was stirred at 100 rpm with an agitator and 540 g of solid sodium chloride was added to the aqueous solution. The solution was also seeded with 36 g of a seed slurry containing 22 g crystal paste and 14 g of a 10% sodium chloride solution. The batch was placed at 4–5° C. to crystallize. 200 ml of the batch was extracted and put in a shaker at 37° C. at the same time. The batches were observed after 24 hours and 48 hours.

The 18 l batch had gelled so that it was almost hard after 24 hours. About 110 ml of the batch was diluted with about 100 ml water and separated in a Sorvall centrifuge after 48 hours of crystallization. The solid phase contained about 47 g of protease and the supernatant contained 160 g of protease. The solid phase was greyish and did not contain any crystals.

The 200 ml sample that had been kept at 37° C. behaved differently. After 24 hours, there were a lot of small needle-shaped crystals and occasional larger regular bulky crystals. The 200 ml batch was spun in a Sorvall centrifuge after 48 hours. The 207.5 g of slurry produced two distinct solids layers containing 54.2 g of paste altogether. The upper, brighter layer contained about 75% of the solids and the lower grayer layer contained about 25%. Both layers contained crystals according to microscopy.

Example 3

Crystallization of a Mutant Protease from *Bacillus subtilis* Using Sodium Sulfate An aqueous solution comprising an ultrafiltrate concentrate of a fermentation broth of a mutant protease derived from the fermentation of *Bacillus subtilis* was prepared as described in Example 1. The resultant aluminum sulfate-treated protease solution was at a concentration of about 55 g/l and crystals that were present were removed by centrifugation.

The pH of the aqueous solution was adjusted to 5.0 using 33% formic acid. A 10 ml batch was given occasional gentle agitation and sodium sulfate was added to a concentration of 20 g/l. The batch was placed at 22° C. for 48 hours. After one day at 22° C., the liquor was full of long needles. No quantification was made. After two days, there were considerably more of the long thin needles.

Example 4

Crystallization of a Mutant Protease from *Bacillus subtilis* Using Sodium Sulfate An aqueous solution comprising an ultrafiltrate concentrate of a fermentation broth of a mutant protease derived from the fermentation of *Bacillus subtilis* was prepared as described in Example 1. The resultant aluminum sulfate-treated protease solution was at a concentration of about 55 g/l and crystals that were present were removed by centrifugation.

The pH of the solution was adjusted to 5.4. Sodium sulfate was added to a 300 ml batch of the protease-containing fermentation broth to a concentration of 60 g/l of salt. The batch was stirred at 100 rpm with an agitator and kept at 30° C. Protease seed crystals were added to the solution. After 21 hours, the liquor was full of uniform sized small rods.

Example 5

Crystallization of a Mutant Protease from *Bacillus subtilis* Usinq Sodium Sulfate in a Semi-Continuous Mode An aqueous solution comprising an ultrafiltrate concentrate of a fermentation broth of a mutant protease derived from the fermentation of *Bacillus subtilis* was prepared as described in Example 1. The resultant aluminum sulfate-treated protease solution was at a concentration of about 55 g/l and crystals that were present were removed by centrifugation.

The pH of the solution was adjusted to 4.8. In the first 1.2 hours, 100 ml of a concentrated sodium sulfate solution was added to a 300 ml batch of the protease-containing fermentation broth to a final concentration of 40 g/l of salt. Seed crystals were added to the batch. The protease was allowed to crystallize at 30° C. overnight.

Beginning at 25 hours, another 300 ml of fresh feed and another 100 ml of concentrated sodium sulfate solution were continuously added over the next three hours. The final batch volume was 800 ml. After a total of 47 hours at 30° C., the liquor contained a large number of medium to large rod shaped crystals.

While the invention has been described in connection with specific embodiments thereof, it will be understood that it is capable of further modifications and this application is intended to cover any variations, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A method for the crystallization of a bacterial or fungal protease enzyme comprising: (a) preparing an aqueous solution containing said protease enzyme; (b) adding sodium sulfate to said aqueous solution in a concentration of between about 0.5% and 10% w/v, wherein step (b) is carried out at a temperature of between about 10° C. and 60° C.; and (c) recovering the crystallized bacterial or fungal protease enzyme.

2. The method according to claim 1, wherein said protease is present in said aqueous solution in a concentration of between about 20 g/l and 80 g/l.

3. The method according to claim 1, wherein said protease is present in said aqueous solution in a concentration of between about 40 g/l and 60 g/l.

4. The method according to claim 1, wherein said sodium sulfate is added in a concentration of between about 1.0% and 7.5% w/v.

5. The method according to claim 1, wherein said sodium sulfate is added in a concentration of between about 1.5% and 4.0% w/v.

6. The method according to claim 1, wherein said step (b) is carried out at a pH of between about 4 and 10.

7. The method according to claim 1, wherein said step (b) is carried out at a pH of between about 4.8 and 5.4.

8. The method according to claim 1, additionally comprising the step of incubating said solution prepared in step (b).

9. The method according to claim 8, wherein said incubation is carried out for a time of between about 1 hour and 10 days.

10. The method according to claim 8, wherein said incubation is carried out for a tine of between about 5 hours and 24 hours.

11. The method according to claim 1 wherein the bacterial protease enzyme is derived from Bacillus.

12. The method according to claim 11 wherein said protease is derived from a *Bacillus subtilis*.

13. The method according to claim 1 wherein said bacterial protease enzyme is derived from the group consisting of Thermomonospora sp., Pseudomonas sp., Clostridium sp., Streptomyces sp., and Micrococcus sp.

14. A method for the crystallization of a bacterial or fungal protease enzyme comprising; (a) preparing an aqueous solution containing said protease enzyme; (b) adding sodium sulfate to said aqueous solution in a concentration of between about 0.5% and 10% w/v, wherein said step (b) is carried out at a temperature of between about 20° C. and 40° C. and at a pH of between about 4.0 and 10.0; (c) allowing crystals of said protease enzyme to form; and (d) recovering the crystallized bacterial or fungal enzyme.

15. The method according to claim 14, wherein said step (b) is carried out at a temperature of between about 22° C. and 30° C.

16. The method according to claim 14, wherein said step (c) is carried out for a time period of between about 2 hours and 48 hours.

17. The method according to claim 14, wherein the bacterial protease enzyme is derived from Bacillus.

18. The method according to claim 14, wherein the fungal protease is derived from Aspergillus or Trichoderma.

19. The method according to claim 14 wherein the bacterial protease enzyme is derived from Bacillus.

20. The method according to claim 19 wherein said protease is derived from a *Bacillus subtilis*.

21. A method for the crystallization of a bacterial or fungal protease enzyme comprising, (a) preparing a protease enzyme solution by removing cells and suspended solids from a fermentation mixture produced by fermentation of a protease producing bacterium or fungus, (b) forming a concentrated solution by concentrating the protease solution wherein the protease is present in a concentration of 20 g/l to 80 g/l, (c) adding sodium sulfate to said concentrated solution in a concentration of between about 0.5% and 10% w/v, wherein step (c) is carried out at a temperature of between about 10° C. and 60° C. and at a pH of between about 4.0 and 10.0, (d) allowing crystal formation of said protease enzyme; and (e) recovering the crystallized protease enzyme.

* * * * *